(12) United States Patent
Stender et al.

(10) Patent No.: US 7,282,331 B2
(45) Date of Patent: Oct. 16, 2007

(54) METHOD FOR IMPROVED SPECIFICITY IN PROBE BASED ASSAYS

(75) Inventors: Henrik Stender, Gentofte (DK); Thais T. Johansen, Concord, MA (US)

(73) Assignee: AdvanDx, Inc., Woburn, MA (US)

( * ) Notice: Subject to any disclaimer, the term of this patent is extended or adjusted under 35 U.S.C. 154(b) by 238 days.

(21) Appl. No.: 10/804,470

(22) Filed: Mar. 18, 2004

(65) Prior Publication Data

US 2005/0032091 A1 Feb. 10, 2005

Related U.S. Application Data

(60) Provisional application No. 60/455,935, filed on Mar. 18, 2003.

(51) Int. Cl.
*C12Q 1/68* (2006.01)
*C07H 21/02* (2006.01)
*C07H 21/04* (2006.01)
*G01N 21/25* (2006.01)

(52) U.S. Cl. .................. 435/6; 536/24.3; 436/164; 436/172

(58) Field of Classification Search ............. None
See application file for complete search history.

(56) References Cited

U.S. PATENT DOCUMENTS

| | | | |
|---|---|---|---|
| 5,532,129 A * | 7/1996 | Heller | 435/6 |
| 5,843,669 A * | 12/1998 | Kaiser et al. | 435/6 |
| 6,207,387 B1 * | 3/2001 | Elsas et al. | 435/6 |
| 6,777,184 B2 * | 8/2004 | Nikiforov et al. | 435/6 |
| 6,872,525 B2 * | 3/2005 | Ishibashi et al. | 435/6 |
| 6,905,827 B2 * | 6/2005 | Wohlgemuth et al. | 435/6 |
| 2001/0046679 A1 * | 11/2001 | Meade et al. | |
| 2002/0090626 A1 * | 7/2002 | Hyldig-Nielsen | 435/6 |
| 2004/0123343 A1 * | 6/2004 | La Rosa | |
| 2004/0146910 A1 * | 7/2004 | Zhou | |

FOREIGN PATENT DOCUMENTS

| | | | |
|---|---|---|---|
| EP | 1033405 | * | 9/2000 |
| WO | WO0066788 | * | 11/2000 |
| WO | WO0173062 | * | 10/2001 |

OTHER PUBLICATIONS

Oliveira et al., Journal of Clinical Microbiology, Jan. 2002, vol. 40, No. 1, pp. 247-251.*
GenBank Accession No. S83568, published Sep. 33, 1993.*
GenBank Accession No. CNS01M9N, published Jun. 14, 2001.*
GenBank Accessio No. BZ846224, published Mar. 13, 2003.*
Relevent pages of EP1033405 has been provided. The document is 344 pages.*
Schutz et al. Clinical Chemistry. 2000. 46:1728-1737.*

* cited by examiner

*Primary Examiner*—Carla Myers
(74) *Attorney, Agent, or Firm*—Stephana E. Patton; Edwards Angell Palmer & Dodge LLP

(57) ABSTRACT

Disclosed are compositions and methods for analyzing a target sequence in a sample. Generally, the method includes use of at least one pair of probes (Probe A and Probe B). In one embodiment, Probe A hybridizes to wanted and unwanted nucleic acid in the sample and bears a fluorophore and Probe B hybridizes to unwanted nucleic acid in the sample and bears a quencher. Fluorescence signal from Probe A hybridizing to unwanted nucleic acid is quenched by any relatively close hybridization of Probe B hereby increasing the specificity for the presence, amount or absence of the wanted target sequence. In preferred embodiments, the method is referred to as Fluorescence In-Situ Hybridization (FISH). The invention has many useful applications including rapidly detecting a microbial target sequence in a clinical sample.

22 Claims, 1 Drawing Sheet

SEQUENCE LISTING

```
<160> NUMBER OF SEQ ID NOS: 10

<210> SEQ ID NO 1
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1
gcttctcgtc cgttc                                                    15

<210> SEQ ID NO 2
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2
acttcaaagg agcaa                                                    15

<210> SEQ ID NO 3
<211> LENGTH: 43
<212> TYPE: DNA
<213> ORGANISM: Staphylococcus schleiferi

<400> SEQUENCE: 3
gagcgaacgg acgaggagct tgctcctttg aagttagcgg cgg                     43
```

<210> SEQ ID NO 4
<211> LENGTH: 43
<212> TYPE: DNA
<213> ORGANISM: Staphylococcus aureus

<400> SEQUENCE: 4
gagcgaacgg acgagaagct tgcttctctg atgttagcgg cgg					43

<210> SEQ ID NO 5
<211> LENGTH: 43
<212> TYPE: DNA
<213> ORGANISM: Staphylococcus schleiferi

<400> SEQUENCE: 5
gagcgaacgg acaaggagct tgctcctttg aagttagcgg cgg					43

<210> SEQ ID NO 6
<211> LENGTH: 43
<212> TYPE: DNA
<213> ORGANISM: Staphylococcus schleiferi

<400> SEQUENCE: 6
gagcgaacgg acaaggagct tgctcctttg aagttagcgg cgg					43

<210> SEQ ID NO 7
<211> LENGTH: 43
<212> TYPE: DNA
<213> ORGANISM: Staphylococcus schleiferi

<400> SEQUENCE: 7
gagcgaacgg acgaggagct tgctcctttg aagttagcgg cgg					43

<210> SEQ ID NO 8
<211> LENGTH: 43
<212> TYPE: DNA
<213> ORGANISM: Staphylococcus schleiferi

<400> SEQUENCE: 8
gagcgaacgg acgaggagct tgctcctttg aagttagcgg cgg					43

<210> SEQ ID NO 9
<211> LENGTH: 43
<212> TYPE: DNA
<213> ORGANISM: Staphylococcus aureus

<400> SEQUENCE: 9
gagcgaacgg acgagaagct tgcttctctg atgttagcgg cgg					43

<210> SEQ ID NO 10
<211> LENGTH: 43
<212> TYPE: DNA
<213> ORGANISM: Staphylococcus aureus

<400> SEQUENCE: 10
gagcgaacgg acgagaagct tgcttctctg atgttagcgg cgg					43

METHOD FOR IMPROVED SPECIFICITY IN PROBE BASED ASSAYS

CROSS-REFERENCE TO RELATED APPLICATION

The present application claims the benefit of priority from U.S. Provisional Application Ser. No. 60/455,935 as filed on Mar. 18, 2003. The disclosure of the 60/455,935 application is incorporated herein by reference.

BACKGROUND OF THE INVENTION

1. Field of the Invention

This invention is related to the field of probe based nucleic acid sequence detection, quantitation and analysis. More specifically, this invention relates to methods and kits, which prevent the generation of false positive results in probe based assays, particularly where said probes are fluorescently labeled PNA or LNA probes.

The invention is more specifically directed to methods and kits suitable for improving the specificity and/or reliability of diagnostic tests using probes. The methods and kits of this invention are particularly well-suited for fluorescence in situ hybridization.

2. Description of the Related Art

Nucleic acid hybridization is a fundamental physiochemical process, central to the understanding of molecular biology. Probe-based assays use hybridization for the detection, quantitation and analysis of nucleic acids. Nucleic acid probes have long been used to analyze samples from a variety of sources for the presence of nucleic acids, as well as to examine clinical conditions of interest in single cells and tissues. More recently, high affinity nucleic acid probe analogs and mimics have become the preferred reagents for hybridization assays.

Locked Nucleic Acid (LNA) and Peptide Nucleic Acid (PNA) are novel high affinity probes which provide higher sensitivity and specificity than conventional DNA probes. DNA is a biological material that plays a central role in the life of living species as the agent of genetic transmission and expression, whereas LNA and PNA are recently developed totally artificial molecules, conceived in the minds of chemists and made using synthetic organic chemistry. Although LNA and PNA can employ common nucleobases (A, C, G, T, and U) and can hybridize to nucleic acids with sequence specificity according to Watson-Crick base paring rules, they differ both structurally and functionally from DNA. Peptide Nucleic Acid, despite its name, is neither a peptide nor a nucleic acid, nor is it even an acid, but a non-naturally occurring polyamide backbone composed of (aminoethyl)-glycine subunits where the nucleobases are connected to the backbone by an additional methylene carbonyl moiety. (See: U.S. Pat. No. 5,539,082 and Egholm et al., Nature 365:566-568 (1993)). Due mostly to the fact that PNA carries a net neutral electrical charge, PNA can form hybrids extremely rapidly and stably with naturally occurring nucleic acids. LNA is a nucleic acid analog created by chemically joining the 2' oxygen and 4' carbon of a ribonucleoside through a methylene linkage. The highly rigid structure of the resultant locked 3'-endo conformation reduces the conformational flexibility of the ribose. The increased rigidity and local organization of the LNA phosphate backbone lowers the entropic penalty for hybridization of LNA probes as compared to DNAs of the same relative composition. These structural features provide PNA and LNA probes with higher affinity for target sequences and furthermore allow PNA and LNA probes to hybridize under conditions that are destabilizing to naturally occurring nucleic acids, such as low salt concentration or in the presence of guanidinium hydrochloride. These attributes enable PNA probes to access targets, such as highly structured rRNA and double stranded DNA, known to be inaccessible to DNA probes (See: Stefano & Hyidig-Nielsen, IBC Library Series Publication #948. International Business Communication, Southborough, Mass., pp. 19-37 (1997), (Fuchs, Appl Envir Micro 64 (12) 4973-82, 1998; Efficient poly(A)+ RNA selection using LNA oligo(T) capture. Technical note, Exiqon A/S, Denmark. LNA and PNA are useful candidates for investigation when developing novel probe-based hybridization assays because of their excellent hybridization features.

Probe based assays are useful in the detection, identification and quantitation of nucleic acids. Nucleic acid probes have long been used to analyze samples for the presence of nucleic acid from a bacteria, fungi, virus or other organism (See for example; U.S. Pat. Nos. 4,851,330, 5,288,611, 5,567,587, 5,601,984 and 5,612,183). Probe-based assays are also useful for examining genetically based clinical conditions of interest. Despite the high specificity of LNA and PNA probes as compared to naturally occurring nucleic acid probes, it is common to encounter sequence regions where it is very difficult to design a probe which allows exclusive detection of the desired target in a particular assay format.

The use of PNA probe mixtures have previously been described as a way to target two adjacent target sequences (US2002058278) as a means to increase specificity, however, that concept required each of the two PNA probes hybridizing the adjacent target sequences to be extended with an arm segment capable of forming a triplex with a third labeled PNA probe, such that a total of three probes were required. In addition, the use of a fourth probe or antibody was proposed.

Blocker probes are nucleic acid or non-nucleic acid probes that can be used to suppress the binding of the probing nucleobase sequence of the probe to an unwanted target sequence. Preferred blocker probes are PNA probes (See: Coull et al., U.S. Pat. No. 6,110,676). Typically blocker probes are closely related to the probing nucleobase sequence and preferably they comprise one or more single point mutations as compared with the probe sought to be detected in the assay. Blocker probes operate by hybridizing to non-target sequences, thereby preventing these sequences from being available for hybridization with the detectable probe. The competition set up between the blocker probe and the detectable probe ensures that each probe will only bind to highly complementary targets, increasing the specificity of the assay. Generally and preferably, blocker probes are directed towards a particular single non-target sequence which differs by at least one nucleobase from the target sequence.

The "Hybridization Probes" method (U.S. Pat. No. 6,174,670) describes use of two DNA probes which hybridize to adjacent target sequences, where one DNA probe is labeled with a fluorophore (donor) and the other DNA probe is labeled with another fluorophore (acceptor), such that simultaneous hybridization of the two probes facilitate Fluorescence Resonance Energy Transfer (FRET). The method teaches that FRET occurs as the energy from the excitation of the donor fluorophore is transferred to the donor fluorophore where it is emitted at the emission wavelength of the donor fluorophore. The combined specificity of the two probes is greater than that of either probe alone, as the detectable signal is dependent on the specific hybridization of two DNA probes. Use of Hybridization Probes is limited to selected donor-acceptor fluorophore pairs and instrumentation, such as the LIGHTCYCLER™, with a special combination of excitation filter for the donor fluorophore and emission filter for the acceptor fluorophore. This method is not directly applicable in, for example, fluorescence in situ hybridization assays using standard fluorescence microscope filter sets.

It would be desirable to have a method for improving the specificity for a target sequence that employs quenching of the fluorescence from binding of fluorophore-labeled probes to unwanted target sequences.

SUMMARY OF THE INVENTION

This invention is directed to methods and kits pertaining to quenching the fluorescence signal from binding of fluorescently detectable probes to unwanted target sequences in hybridization assays.

It has been surprisingly observed that the signal caused by the binding of fluorophore-labeled probes to unwanted target nucleic acid sequences can be dramatically suppressed by the use of quencher labeled probes wherein the sequence is complementary to a target sequence on the unwanted DNA or RNA adjacent to the target sequence which the detectable probe binds, provided that there exists at least one nucleobase difference between the wanted and unwanted target. For example, it has been observed that the addition of a quencher labeled PNA probe eliminated the fluorescence from the binding of labeled PNA probe to an unwanted target sequence (see Example 1).

The method includes a pair of probes (Probe A and Probe B), wherein Probe A is comprised of a nucleotide sequence hybridizing to a target region of both wanted and unwanted DNA or RNA and is labeled with a fluorophore at the end which, upon hybridization is closest to the adjacent target region for Probe B; Probe B is comprised of a nucleotide sequence hybridizing to a target region of unwanted DNA or RNA adjacent to the target region of Probe A and is labeled with quencher at the end which, upon hybridization is closest to the adjacent target region for Probe A, said fluorophore and quencher being the donor moiety and acceptor moiety, respectively, for fluorescence resonance energy transfer. Preferably, Probe A and Probe B are high affinity probes. Most preferable, Probe A and Probe B are PNA probes.

Accordingly, and in one aspect, the invention features a method to analyze a target sequence in a sample. In one embodiment, the method includes contacting the sample with at least one pair of probes (called Probe A and Probe B for convenience). In a more specific embodiment, the two probes are characterized as follows: i) Probe A is comprised of a nucleotide sequence, which hybridizes to a target region of both wanted and unwanted DNA or RNA and is labeled with a fluorophore at the end which, upon hybridization is closest to Probe B; and ii) Probe B is comprised of a nucleotide sequence which hybridizes to the target region of unwanted DNA or RNA adjacent to the target region of Probe A and is labeled with a quencher at the end which, upon hybridization is closest to Probe A. Preferably, the method further includes detecting, identifying or quantitating the hybridization of Probe A to the target sequence, under suitable hybridization conditions, wherein the presence or amount of wanted DNA or RNA present in the sample can be positively correlated with the fluorescence of the fluorophore of Probe A.

Practice of the invention is flexible and can be adapted as needed to suit an intended invention objective. Thus, one or more of the foregoing hybridization steps, for instance, can be accomplished in nearly any order provided intended results are achieved.

As should be apparent, use of a wide variety of probes and/or probe pairs is contemplated. For instance, use can entail employment of an addition of about 1, 2, 3, or about 4 pairs of probes (Probe A″ and Probe B″). In such invention embodiments, the fluorophore of each probe A″ is typically selected to emit at a particular light emission wavelength that is identifiable with (and preferably unique to) the presence of a specific fluorophore. A variety of suitable probes can be used to practice the invention including those specifically mentioned herein. In embodiments in which use of multiple probe mixtures are envisioned, generally the sequence of each probe therein will be different from the two probes referred to above as Probe A and Probe B.

As discussed, the present invention method is readily adapted to include one or more additional probe pairs, for instance, Probe A and Probe B alone; Probe A and Probe B with Probe A″ and Probe B″. Choice of a particular probe configuration will be guided by recognized parameters such as characteristics of the target sequence to be detected and need to achieve a desired detection result (eg., identification and quantitation of multiple target sites in a sample). However, it will often be more preferred to use a single probe pair (Probe A and Probe B) to help minimize assay complexity and help analyses of results It will be appreciated that an important feature of the present invention is that the fluorophore of Probe A, for instance, will be detectable under conditions in which Probe B cannot hybridize near the site to which Probe A is bound. That is, the Probe B cannot bind to wanted DNA or RNA or at least cannot hybridize specifically enough thereto to impact functionality of the Probe A fluorophore. A related feature of importance is that when Probe B, for instance, hybridizes to target in a way that is sufficient to position the quencher relatively close to the fluorophore of Probe A, light emission from the fluorophore is reduced and often quenched completely. Thus, in situations where there is target sequence of interest, Probe A is generally detectable by the user. However, when the target sequence is of unwanted DNA, Probe A is much more difficult to detect and is often quenched completely. Of course, when there is no target sequence, Probe A is also undetectable by the method.

Preferred positions between fluorophore and quencher will be generally sufficient to support detectable FRET as determined, for instance, by methods disclosed herein. Typically, such "close" positions will space the fluorophore and quencher less than about 10 nucleotides apart, preferably less than 8 nucleotides apart, more preferably about 0 to about 5 nucleotides apart. In these instances, light emission from the Probe A will be reduced substantially and in some cases quenched entirely. Put another way, the functionality of the Probe A fluorophore, for instance, will be much less, and result in the generation of little or no signal from that probe. This capacity to produce a spatially responsive and detectable signal in the presence of target sequence is an important feature of the invention that provides many advantages including, but not limited to, a relatively rapid and sensitive target detection assay. An example of the method is shown in FIG. 1.

The invention also features a kit that includes at least a Probe A comprised of a nucleotide sequence, which hybridizes to a target region of both wanted and unwanted DNA or RNA and is labeled with a fluorophore at the end which, upon hybridization is closest to the adjacent target region for Probe B; and a Probe B comprised of a nucleotide sequence which hybridizes to unwanted target DNA or RNA adjacent to the target region of Probe A and is labeled with a quencher at the end which, upon hybridization is closest to Probe A.

Thus in one embodiment, the invention provides a kit suitable for performing an assay which detects the presence, absence or amount of target sequence in a sample. In one embodiment, the kit includes, for instance, a Probe A that includes a nucleotide sequence, which preferably hybridizes to a target region of both wanted and unwanted DNA or RNA and is labeled with a fluorophore at the end which, upon hybridization is closest to the adjacent target region for Probe B. Preferably, the kit further provides a Probe B that typically includes a nucleotide sequence which preferably hybridizes to the target region of unwanted DNA or RNA adjacent to the target region of Probe A. More preferred probes (Probe B) are suitably labeled with a quencher at the end which, upon hybridization is closest to Probe A.

The invention provides additional advantages.

The method can be used to suppress the fluorescence from binding of a fluorophore-labeled probe to unwanted targets in situations where the probe does not provide sufficient discrimination between wanted target and unwanted target sequences, but where the adjacent target sequences can be used to distinguish between wanted target and unwanted targets. The quencher-labeled probe will then hybridize to the unwanted target sequences, but not to the wanted target sequence, hereby quenching the fluorescence from the fluorophore-labeled probes hybridized to the unwanted target.

As an important aspect of the invention, the quencher-labeled probe hybridizes to the unwanted target but not to the wanted target hereby eliminating unwanted signal without interfering with the fluorescent signal generated from the binding of the fluorescent-labeled probe to the wanted target. Fluorescence resonance energy transfer (FRET) is therefore used as a means to remove fluorescent signal for hybridization to unwanted target DNA or RNA, but not as a means to measure hybridization to the wanted target sequence. The method does therefore not require special instrumentation or filters designed for measuring FRET and can be directly applied to, for example, fluorescence in situ hybridization assays using standard fluorescence microscope filter sets. Similarly, the method can be used with conventional fluorophores as long as the fluorescent signal can be quenched by conventional quenchers and as such does not require special sets of donor-acceptor pairs.

The quencher-labeled probe does not need to be specific for the particular unwanted target, but may be complementary to a target sequence present in several other unwanted targets as longs as it is not complementary to the target sequence of the wanted target. This way the method obtains its specificity from nucleobase differences from two adjacent target sequences and hereby facilitates and/or improves the method for designing specific probes and may not only lead to improved specificity of existing assays using a single probe, but may also enable design of probes where neither Probe A nor Probe B provide sufficient specificity, but where the use of the two probes in accordance with this invention leads to optimal specificity.

In particular, this invention can eliminate some of the limitations of previously published PNA probes. For example, the cross-hybridization of a PNA probe targeting *Staphylococcus aureus* rRNA to *Staphylococcus schleiferi* rRNA (see Oliveira et al., *J. Clin. Microbiol.* 40:247-251 (2002)) can be eliminated using a quencher-labeled PNA probe targeting an adjacent sequence on *Staphylococcus schleiferi* rRNA as outlined in Example 1.

The invention is flexible and can be used in one or a combination of suitable probe formats. In one embodiment, the quencher-labeled probe (Probe B) also has a fluorophore at the opposite end of the probe. Preferably, and in this embodiment, the fluorophore on Probe B differs from the fluorophore on Probe A. Presence of the fluorescent signal will then depend on whether just one or both probes are bound. For example, in an embodiment in which Probe B is labeled with fluorescein (green) and a quencher at opposite ends and targeting a unique target sequence whereas Probe A is labeled with rhodamine (red) and targeting an adjacent universal sequence. The signal will then be red for DNA or RNA that do not have the unique sequence whereas the signal for DNA or RNA with the unique target sequence will be green, only, as the red signal will be quenched. This approach is particularly well-suited for design of dual-color assays with inherent negative controls and in particularly fluorescence in situ hybridization assays using multiband filters. The approach is also well-suited for analysis of single nucleotide polymorphisms where Probe A targets a non-polymorphic sequence (equivalent to the wanted and unwanted target) and Probe B targets a polymorphic sequence (equivalent to the unwanted target).

DESCRIPTION OF THE PREFERRED EMBODIMENTS

Figure 1:
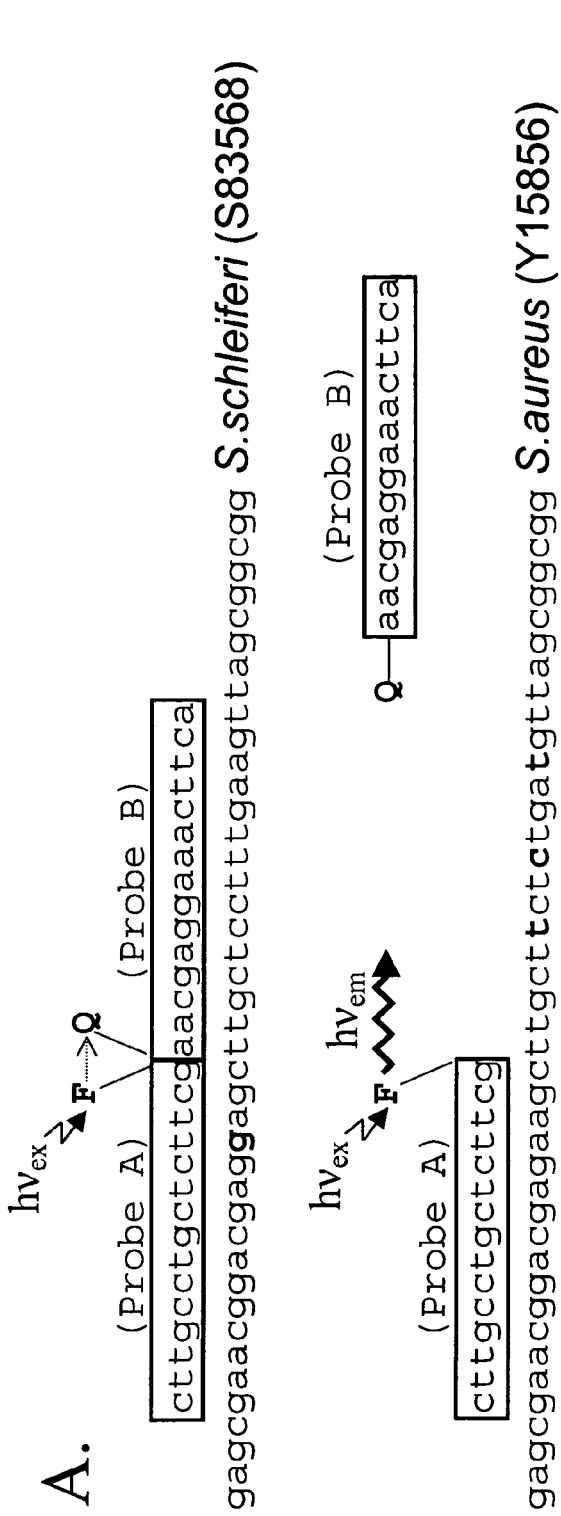
FIG. 1B shows alignment of partial 16S rRNA sequences of *Staphylococcus schleiferi* (GenBank accession number AB009945) (SEQ ID NO: 5), *Staphylococcus schleiferi* (GenBank accession number 83372) (SEQ ID NO: 6), *Staphylococcus schleiferi*(GenBank accession number S83568) (SEQ ID NO: 7), *Staphylococcus schleiferi*(GenBank accession number Z26904) (SEQ ID NO: 8), *Staphylococcus aureus* (GenBank accession number Y15856) (SEQ ID NO: 9), *Staphylococcus aureus* (GenBank accession number AF076030) (SEQ ID NO: 10). Differences between nucleobase sequences of *Staphylococcus aureus* and corresponding nucleobase sequences of *Staphylococcus schleiferi* are indicated by characters in bold over shaded boxes. Notice that the upper two strains of *Staphylococcus schleiferi* differ from the lower two strains by one base.
In FIG. 1A, the anti-parallel hybridization of the probe nucleobase sequence GCT-TCT-CGT-CCG-TTC (SEQ ID NO: 1) (Probe A) to both the wanted target sequence of *Staphylococcus aureus* (SEQ ID NO: 4) and to the unwanted target sequence of *Staphylococcus schleiferi* (SEQ ID NO: 3) and of the probe nucleobase sequence ACT-TCA-AAG-GAG-CAA (SEQ ID NO: 2) (Probe B) to the adjacent, unwantedtarget sequence of *Staphylococcus schleiferi* are illustrated. The two nucleobase sequences are labeled with fluorescein (F) and dabcyl (Q), respectively, at adjoining ends. The figure demonstrates how both Probe A and Probe B will bind to the *Staphylococcus schleiferi* target, but only Probe A will bind to the *Staphylococcus aureus* target. Note that even though there is a one base mismatch between Probe A probe and the *Staphylococcus schleiferi* target sequence, a relatively stabile hybrid is formed. This stability is due in part to the total length of the probe (15 bases), and to the relatively high stability of G-T pairs (mismatches) as compared to all other PNA-NA mismatch hybrids.

I. Definitions:

a. As used herein, the term "nucleobase" means those naturally occurring and those non-naturally occurring heterocyclic moieties commonly known to those who utilize nucleic acid technology or utilize peptide nucleic acid technology to thereby generate polymers that can sequence specifically bind to nucleic acids.

b. As used herein, the term "nucleobase sequence" means any segment of a polymer that comprises nucleobase containing subunits. Non-limiting examples of suitable polymers or polymers segments include oligodeoxynucleotides, oligoribonucleotides, peptide nucleic acids, locked nucleic acid, nucleic acid analogs, nucleic acid mimics, and/or chimeras c. As used herein, the term "target sequence" means the nucleobase sequence that is to be detected by the probe. The term "wanted target sequence" refers to the target sequence of interest, i.e. the sequence which the assay was designed to detect, whereas "unwanted target sequence" refers to a target sequence detected, but not of interest. As used herein, the term "probe" means a polymer (e.g. a DNA, RNA, PNA, LNA chimera, linked polymer as well as combinations thereof (eg., an LNA/DNA chimera)) having a probing nucleobase sequence that is designed to sequence specifically hybridize to a target sequence of a of interest.

d. As used herein, "analyzed" means that the individual bacteria are marked for detection, identification and/or quantitation.

e. As used herein, the term "high affinity probe" means a probe with improved hybridization properties as compared to conventional deoxynucleic acid (DNA) probes. More specifically, a high affinity probe corresponds in sequence with a particular DNA probe, however the high affinity probe has improved hybridization characteristics as determined eg., by measuring the melting point (Tm). As an example, a DNA probe which has been modified with at least one LNA unit or a PNA probe will be a high affinity probe. Other examples will be apparent from the discussion herein.

f. As used herein, the term "peptide nucleic acid" or "PNA" means any oligomer, linked polymer or chimeric oligomer, comprising two or more PNA subunits (residues), including any of the polymers referred to or claimed as peptide nucleic acids in U.S. Pat. Nos. 5,539,082, 5,527,675, 5,623,049, 5,714,331, 5,736,336, 5,773,571, 5,786,461, 5,837,459, 5,891,625, 5,972,610, 5,986,053, 6,107,470 and 6,357,163. In the most preferred embodiment, a PNA subunit consists of a naturally occurring or non-naturally occurring nucleobase attached to the aza nitrogen of the N-[2-(aminoethyl)] glycine backbone through a methylene carbonyl linkage.

g. As used herein, the term "locked nucleic acid" or "LNA" means any oligomer, linked polymer or chimeric oligomer, comprising one or more LNA subunits (residues), including any of the polymers referred to or claimed as locked nucleic acids, and nucleic acid analogs in U.S. Pat. Nos. 6,639,059, 6,670,461, United States Patent Application numbers US2003077609 A1, US2003224377 A, US2003082807 A1 and World Patent Office Document number WO03095467. In the most preferred embodiment, a LNA subunit consists of a naturally occurring or non-naturally occurring ribonucleoside in which the 4' oxygen is joined to the 2' carbon through a methylene linkage.

h. An "end" of a probe as disclosed herein means the 5' or 3' end (amino terminus or carboxyl terminus of PNA probes) unless specified otherwise. Reference herein to "internal" probe nucleobases (as in labeling a probe internally, for instance), means not at the end of a probe, ie., one or more nucleobases between the ends of that probe.

DETAILED DESCRIPTION OF THE INVENTION

General:

PNA Synthesis:

Methods for the chemical assembly of PNAs are well known (see: U.S. Pat. Nos. 5,539,082, 5,527,675, 5,623,049, 5,714,331, 5,736,336, 5,773,571, 5,786,461, 5,837,459, 5,891,625, 5,972,610, 5,986,053 and 6,107,470).

LNA Synthesis:

Methods for the chemical assembly of LNAs are well known (see: Patent Nos. US2003077609 A1, US2003224377 A1, US2003082807 A1 and World Patent Office Document number WO03095467)

PNA Labeling:

Preferred non-limiting methods for labeling PNAs are described in U.S. Pat. No. 6,110,676, 6,361,942, 6, 355,421 or are otherwise well known in the art of PNA synthesis and peptide synthesis.

LNA Labeling:

Preferred non-limiting methods for labeling LNAs are described in U.S. Pat. Nos. 6,639,059, 6,670,461, United States Patent Application numbers US2003077609 A1, US2003224377 A1, US2003082807 A1 and World Patent Office Document number WO03095467 or are otherwise well known in the art of LNA synthesis.

Labels:

Fluorophores are the detectable moieties suitable for labeling probes of this invention. Preferred fluorochromes (fluorophores) include 5 (6)-carboxyfluorescein (Flu), 6-((7-amino-4-methylcoumarin-3-acetyl) amino) hexanoic acid (Cou), 5 (and 6)-carboxy-X-rhodamine (Rox), Cyanine 2 (Cy2) Dye, Cyanine 3 (Cy3) Dye, Cyanine 3.5 (Cy3.5) Dye, Cyanine 5 (Cy5) Dye, Cyanine 5.5 (Cy5.5) Dye Cyanine 7 (Cy7) Dye, Cyanine 9 (Cy9) Dye (Cyanine dyes 2,3,3.5,5 and 5.5 are available as NHS esters from Amersham, Arlington Heights, Ill.), JOE, Tamara or the Alexa dye series (Molecular Probes, Eugene, Oreg.).

Fluorescence quenchers are the acceptor moieties suitable for labeling quencher probes of this invention. The preferred quencher is 4-((-4 (dimethylamino)phenyl)azo)benzoic acid (dabcyl).

Other suitable labeling reagents and preferred methods of attachment would be recognized by those of ordinary skill in the art of PNA, peptide or nucleic acid synthesis.

Spacer/Linker Moieties:

Generally, spacers are used to minimize the adverse effects that bulky labeling reagents might have on hybridization properties of probes. Linkers typically induce flexibility and randomness into the probe or otherwise link two or more nucleobase sequences of a probe. Preferred spacer/linker moieties for the nucleobase polymers of this invention consist of one or more aminoalkyl carboxylic acids (e.g. aminocaproic acid) the side chain of an amino acid (e.g. the side chain of lysine or omithine) natural amino acids (e.g. glycine), aminooxyalkylacids (e.g. 8-amino-3,6-dioxaoctanoic acid), alkyl diacids (e.g. succinic acid), alkyloxy diacids (e.g. diglycolic acid) or alkyldiamines (e.g. 1,8-diamino-3, 6-dioxaoctane).

Hybridization Conditions/Stringency:

Those of ordinary skill in the art of nucleic acid hybridization will recognize that factors commonly used to impose or control stringency of hybridization include formamide concentration (or other chemical denaturant reagent), salt concentration (i.e., ionic strength), hybridization temperature, detergent concentration, pH and the presence or absence of chaotropes. Optimal stringency for a probe/target sequence combination is often found by the well known technique of fixing several of the aforementioned stringency factors and then determining the effect of varying a single stringency factor. The same stringency factors can be modulated to thereby control the stringency of hybridization of a PNA or LNA to a nucleic acid, except that the hybridization of a PNA is fairly independent of ionic strength. Optimal stringency for an assay may be experimentally determined by examination of each stringency factor until the desired degree of discrimination is achieved.

Suitable Hybridization Conditions:

Generally, the more closely related the background causing nucleic acid contaminates are to the target sequence, the more carefully stringency must be controlled. Blocking probes may also be used as a means to improve discrimination beyond the limits possible by mere optimization of stringency factors. Suitable hybridization conditions will thus comprise conditions under which the desired degree of discrimination is achieved such that an assay generates an accurate (within the tolerance desired for the assay) and reproducible result.

Aided by no more than routine experimentation and the disclosure provided herein, those of skill in the art will easily be able to determine suitable hybridization conditions for performing assays utilizing the methods and compositions described herein. Suitable in-situ hybridization or PCR conditions comprise conditions suitable for performing an in-situ hybridization or PCR procedure.

Hybridization Characteristics:

The hybridization characteristics of a probe are usually described by the melting point (Tm) of the probe-target hybrid. The melting point is therefore an important parameter used to guide the experimentation described above to determine the suitable hybridization conditions. However, when the assay is dependent on simultaneous hybridization of two probes each of these two probes must to be designed with similar hybridization characteristics such that the same hybridization conditions are suitable for both probes. The length of the nucleobase sequence provides a rough assessment of the hybridization characteristics, but can be refined by calculating the Tm using on-line calculators available at www.applied biosystems.com. The degree of similarity between the hybridization characteristics of Probe A and Probe B is dependent on both the stringency of the hybridization conditions and the desired degree of discrimination that needs to be achieved. Aided by no more than routine experimentation and the disclosure provided herein, those of skill in the art will easily be able to determine the degree of similarity required for performing assays utilizing the methods and compositions described herein.

Blocker Probes:

Blocker probes are nucleic acid or non-nucleic acid probes that can be used to suppress the binding of the probing nucleobase sequence of the probing polymer to a non-target sequence. Preferred blocking probes are PNA probes (See: Coull et al., U.S. Pat. No. 6,110,676).

Typically blocker probes are closely related to the probing nucleobase sequence and preferably they comprise one or more single point mutations as compared with the probe sought to be detected in the assay. It is believed that blocker probes operate by hybridization to the non-target sequence to thereby form a more thermodynamically stable complex than is formed by hybridization between the probing nucleobase sequence and the non-target sequence. Formation of the more stable and preferred complex blocks formation of the less stable non-preferred complex between the probing nucleobase sequence and the non-target sequence. Thus, blocker probes can be used with the methods, kits and compositions of this invention to suppress the binding of the nucleic acid or non-nucleic acid probe to a non-target sequence that might be present and interfere with the performance of the assay.

Probing Nucleobase Sequence:

The probing nucleobase sequence of a probe of this invention is the specific sequence recognition portion of the construct. Therefore, the probing nucleobase sequence is a nucleobase sequence designed to hybridize to a specific target to directly or indirectly detect the presence, absence or amount of the target sequence of interest in a sample. Consequently, with due consideration to the requirements of a probe for the assay format chosen, the length and sequence composition of the probing nucleobase sequence of the probe will generally be chosen such that a stable complex is formed with the target sequence under suitable hybridization conditions.

Detection, Identification and/or Quantitation:

Detection is meant analysis for the presence or absence of the target sequence optionally present in the sample. Identification is meant establishment of the identity of the target sequence. By quantitation is meant measuring the amount of target sequence in a sample. Some assay formats provide simultaneous detection, identification and enumeration (for example see Stender, H. et al., *J. Microbiol. Methods.* 45:31-39 (2001), others provide detection and identification (for example see Stender, H. et al., *Int. J. Tuberc. Lung Dis.* 3:830-837 (1999) and yet other assay formats only provide identification (for example see Oliveira, K et al. *J. Clin. Microbiol.* 40:247-251 (2002)).

As discussed above, the invention features a method for the analysis of a target sequence in a sample (typically a sample of biological origin). In one embodiment, the method includes contacting the sample with at least one pair probes (Probe A and Probe B), in which i) Probe A includes a nucleotide sequence, which hybridizes to a target region of both wanted and unwanted DNA or RNA and is labeled with a fluorophore at the end which, upon hybridization is closest to Probe B; and ii) Probe B includes a nucleotide sequence which hybridizes to the target region of unwanted DNA or RNA adjacent to the target region of Probe A and is labeled with a quencher at the end which, upon hybridization is closest to Probe A. Preferred methods also include a step b that detects, identifies or quantitates hybridization of Probe A to the target sequence, under suitable hybridization conditions. The presence or amount of the wanted DNA or RNA present in the sample can be positively correlated with the fluorescence of the first fluorophore of Probe A.

In many embodiments, the method will be performed with a suitable control sample that will typically include all components of the experimental sample referred to above except that target sequence will not be present. Alternatively, one or more of the probes will not be present. In another embodiment, the control sample will include a defined amount of one or more target sequences. Use of such control sample can provide a useful "baseline" signal for performing the method optimally. However, it will be appreciated that once the characteristics of a particular sample (or set of samples such as encountered in a clinic) is known, use of a control sample may not be needed. When the control sample is used, it can be handled before, during or after manipulation of the experimental sample.

By the phrase "positively correlated" means that any signal obtained from the experimental sample can be related to the presence or amount of wanted DNA or RNA linearly for example. Typically, the positive correlation will be made by reference to a suitable control sample as discussed above. The correlation can be made by inspection (eg., graphically) or in most cases will be made by automated or semi-automated methodologies that are standard in the field and discussed herein.

Thus in one invention embodiment, the method of the invention is performed by fluorescence in situ hybridization. If desired, Probe A and Probe B can be high affinity probes such as those comprising LNA, PNA or both. In some instances, the probes will be entirely composed of PNA or LNA, for instance.

Nearly any probe sequence can be used to practice the invention. However, the most useful probe sequences are known to hybridize to a desired wanted or unwanted DNA or RNA sequence. Preferred probe sizes will be generally less than about 30 nucleobases, preferably less then about 20 nucleobases, more preferably between from about 8 to 18 nucleobases with between from about 11 to about 16 nucleobases (subunits) being preferred for many applications.

For example, the Probe A can include the following nucleotide sequence: GCT-TCT-CGT-CCG-TTC (SEQ ID NO: 1) and/or the Probe B can include the following nucleotide sequence: ACT-TCA-AAG-GAG-CAA (SEQ ID NO: 2). In this embodiment, the probes can include other nucleobases (eg., less than about 10, preferably less than about 5, usually one or two nucleobases), provided such additions do not detectably impact function of the probes.

However, in embodiments in which hybridization specificity is especially important, Probe A can consist essentially of the following nucleotide sequence: GCT-TCT-CGT-CCG-TTC (SEQ ID NO: 1) and the first fluorophore and/or the Probe B can consist essentially of the following nucleotide sequence: ACT-TCA-AAG-GAG-CAA (SEQ ID NO: 2) and the quencher.

Where even more potential hybridization specificity is desired, the Probe A can consist of the following nucleotide sequence: GCT-TCT-CGT-CCG-TTC (SEQ ID NO: 1) and the fluorophore. Also, the Probe B can consist of the following nucleotide sequence: ACT-TCA-AAG-GAG-CAA (SEQ ID NO: 2) and the quencher. In this embodiment, the Probe A is labeled with the fluorophore at the probe terminus closest to the binding site of Probe B, and Probe B is labeled with a quencher at the probe terminus closest to the binding site of Probe A.

As discussed, practice of the invention is flexible and provides for internal labeling of Probes A and B typically with at least one detectable nucleoside analogue. Examples include nucleosides bearing one or more suitable radionucleosides, biotinylated nucleosides, etc.

In a further embodiment of the foregoing invention method, the Probe B is further labeled with a fluorophore at the opposite end and which has a different emission spectrum than the fluorophore on Probe A.

In embodiments in which Probe A and Probe B are LNA or PNA probes such probes will be desirably separated by a distance of between from about one to about five nucleobases bases. In this invention example, FRET analysis is supported by the relatively close potential spacing between the fluorophore on Probe A and quencher on Probe B after hybridization to target.

Practice of the invention is compatible with a wide range of target sequences. Such sequences can be obtained from nearly any biological sample (eg., cell or tissue) using standard isolation methods such as those routinely used to purify nucleic acids. For instance, and in certain embodiments, it will be desirable to manipulate a particular cell or tissue sample to preserve (stabilize) nucleic acids therein. Methods of performing such manipulations are known in the field and include, but are not limited to, fixation, decreasing temperature (eg., freezing), desiccation, and binding nucleic acid to a solid support specifically.

The method can be adapted as needed to suit an intended invention objective. For instance, and in one embodiment, step (b) of the method can be used to detect, identify, and/or quantitate the presence or amount of at least one species of a microorganism in the sample. In one embodiment, the detection, identification or quantitation step is indicate of a condition of medical interest (eg., infection, and genetically based diseases such as those described below).

Additionally, the method of this invention can be used to hybridize target sequence that has been obtained from a biological sample that has been subjected to drug exposure. Examples include an antimicrobial agent such as a antibiotic; antifungal, antiviral (eg., nucleoside analogue, protease inhibitor, etc), as well as drug intended to kill or inhibit the growth of various parasites such as nematodes and protozoa. For instance, and in one embodiment, the target sequence is isolated from a microorganism exposed to at least one antimicrobial agent and the presence of amount of wanted DNA or RNA is taken to be indicative of an effect of the antimicrobial agent on the microorganism. Examples of such drugs are known in the field. See eg., The *Pharmacological Basis of Therapeutics* (L. S. Goodman and A. Gilman Eds) ($6^{th}$ Ed. Macmillan Publishing Co., New York, N.Y.)

As also discussed, the invention features a kit suitable for performing an assay which detects the presence, absence or amount of target sequence in a sample. A preferred kit includes a Probe A comprised of a nucleotide sequence, which preferably hybridizes to a target region of both wanted and unwanted DNA or RNA and is labeled with a fluorophore at the end which, upon hybridization is closest to the adjacent target region for Probe B. Also preferably, the kit further includes a Probe B comprised of a nucleotide sequence which hybridizes to the target region of unwanted DNA or RNA adjacent to the target region of Probe A and is labeled with a quencher at the end which, upon hybridization is closest to Probe A. Further kit components optionally include water, one or more buffers, stabilizers and the like as well as directions for using the kit.

In embodiments in which the kit includes Probe A, Probe B or both the probe(s) will have a structure already described above.

Kits according to the invention can be adapted for use as needed to serve a particular detection, identification and/or quantitation goal. In particular, a kit is "adapted for" a use if it includes at least one probe mixture intended to detect, quantify, and/or identify a particular target sequence. Choice of a specific probe mixture will be guided by recognized parameters such as the target sequence to be analyzed, sensitivity desired, choice of fluorophore, etc. Of course, a kit can be "adapted for" use in other ways including appropriate selection of control samples, buffers, etc. that are known to be particularly effective in the detection, identification or quantitation of a particular target sequence.

Thus in one kit embodiment, the kit is adapted for use in a fluorescence in-situ hybridization assay. As discussed, use of invention is not tied to any specific sample. Thus in one embodiment, the kit is adapted to detect organisms in food, beverages, water, pharmaceutical products, personal care products, dairy products or environmental samples. Other kits of the invention are adapted to test raw materials, products or processes. Still other kit embodiments are adapted to examine clinical samples (eg., those from patients having or suspected of having a microbial or viral infection). In this embodiment, the clinical samples can be from nearly any source including clinical specimens (or equipment, fixtures and products used to treat humans or animals. More specific examples of suitable specimens in this regard include blood, sputum, stool, tissue, pus, saliva, semen, vaginal or eye secretions, etc.)

In other embodiments, a suitable kit in accord with the invention is adapted to detect a target sequence which is specific for a genetically based disease or is specific for a predisposition to a genetically based disease. In this invention example, the target sequence can be associated with a disease selected from the group consisting of 5-Thalassemia, sickle cell anemia, Factor-V Leiden, cystic fibrosis and cancer related targets such as p53, pIO, BRC-1 and BRC-2.

In other kit embodiments, the kit is adapted to detect a target sequence in a forensic technique. Examples of such techniques include prenatal screening, paternity testing, identity confirmation or use of conventional techniques associated with a crime investigation. In these invention embodiments, the kit is preferably adapted by designing probes that hybridize well to target sequence from the individual of forensic interest.

Other uses, advantages and embodiments of the invention are described below.

PREFERRED EMBODIMENTS OF THE INVENTION

Pairs of Probes:

The method and kits disclosed herein comprises the use of two probes with nucleobase sequences that hybridize to adjacent target sequences of an unwanted DNA or RNA, where at least one target sequence includes at least one nucleobase difference between wanted and unwanted DNA or RNA. Also typically, the method requires that the two nucleobase sequences have similar hybridization characteristics under suitable hybridization conditions.

Suitable probes for use with the invention feature, upon hybridization, a separation between the two probes of a distance of less then about ten nucleotide base pairs, preferably about one to five nucleotide bases as long as energy transfer occurs. More preferably, there is no separation between the two probes, ie. the probes are adjacent to one another.

As will be appreciated to those familiar with the art, the invention is not tied to the use of any particular fluorophore and many known in the field will be suitable for a variety of application. In one embodiment, an acceptable fluorophore for use with the invention is selected from the group consisting of 5(6)-carboxyfluorescein, 5-(2'-aminoethyl)-aminonaphthalene-1-sulfonic acid (EDANS), bodipy, rhodamine, Cy2, Cy3, Cy 3.5, Cy5, Cy5.5 and texas red. Appropriate quenching entities are also known and include, but are not limited to 4-((-4-(dimethylamino)phenyl)azo) benzoic acid (dabcyl).

As also discussed, the probes disclosed herein can include one or more spacer moieties linked to one or both of the donor and acceptor moieties to the end of the probes to which it/they is/are linked. A typical spacer moiety includes one or more linked amino acid moieties.

A variety of probes and probe pairs can be used with the invention provided intended detection results are achieved. This invention pertains to methods and kits using pairs of probes where the pairs of probes efficiently transfer energy between the fluorophore and the quencher linked to adjoining ends of two probes hybridized to adjacent target sequences of unwanted DNA or RNA leading to fluorescence quenching. Preferably the probes are high affinity probes and most preferably the probes are PNA probes. Those skilled in the art will understand that mixtures of probe types, i.e. where Probe A is PNA, and Probe B is an LNA, can also be used.

In one embodiment, this invention is directed to pairs of PNA probes suitable for the analysis of *Staphylococcus aureus* optionally present in a sample where unwanted hybridization of the labeled probe to *Staphylococcus schleiferi* rRNA is quenched by hybridization of a quencher-labeled probe hybridizing to *Staphylococcus schleiferi* rRNA, but not to *Staphylococcus aureus* rRNA. General characteristics (e.g. length, labels, nucleobase sequences, linkers etc.) of PNA probes suitable for the detection, identification and/or quantitation of *Staphylococcus aureus* have been previously described herein. The preferred probing nucleobase sequence of the pairs of PNA probes (Probe A and Probe B) of this invention are listed in the table below.

| Sequence ID | Nucleobase sequence |
|---|---|
| Probe A (Seq. Id. No. 1) | GCT-TCT-CGT-CCG-TTC |
| Probe B (Seq. Id. No. 2) | ACT-TCA-AAG-GAG-CAA |

Also envisioned are the complementary sequences and variations of the particular sequences and complementary sequences. Variations of the probing nucleobase sequences within the parameters described herein are considered to be an embodiment of this invention. Common variations include, deletions, insertions and frame shifts. Additionally, a shorter probing nucleobase sequence can be generated by truncation of the sequence identified above.

The probes of this invention will comprise at least the probing nucleobase sequence (as previously described herein) and a fluorophore or a quencher, but may comprise additional moieties. Non-limiting examples of additional moieties include linkers, spacers, natural or non-natural amino acids, or other subunits of PNA, LNA, DNA or RNA.

Methods:

The present invention is flexible and can be used in one or a combination of suitable formats. The preferred embodiments, the method of this invention are used in fluorescence in-situ hybridization (FISH) assays, where the quencher-labeled probe is used to quench the signal from the hybridization of the fluorophore-labeled probe to unwanted target sequence.

Because the of PNA probes of this invention can be designed to be stable to the enzymes found in the cell, this method is particularly well suited to detecting a target sequence in a cell, tissue or organism, whether living or not. Thus, in preferred embodiments, fluorescence in-situ hybridization is used as the assay format for detecting identifying or quantitating target organisms. Most preferably, fluorescence in-situ hybridization (FISH or PNA-FISH) is the assay format. Exemplary methods for performing PNA-FISH can be found in: Thisted et al. Cell Vision, 3:358-363 (1996) or WIPO Patent Application WO97/18325, herein incorporated by reference.

Microorganisms and human cells can be analyzed with the pair of probes according to this invention and detected by several exemplary methods. The cells can be fixed on slides and then visualized with a microscope or laser scanning device. Alternatively, the cells can be fixed and then analyzed in a flow cytometer (See for example: Lansdorp et al.; WIPO Patent Application; WO97/14026). Slide scanners and flow cytometers are also useful for rapidly quantitating the number of target organisms present in a sample of interest.

Methods of the invention have a wide spectrum of useful applications including use to detect, identify, or quantitate the presence or amount of a microorganisms or viruses in the sample. Alternatively, or in addition, the method is used to detect, identify, or quantitate the presence or amount of one or more species of a microorganism in the sample. For instance, the method can be used to determine the effect of antimicrobial agents on the growth of one or more microorganisms in the sample. Also, such methods can be used to determine the presence or amount of a taxonomic group of microorganisms in the sample. The methods also find use in diagnosis of a condition of medical interest.

When performing the method of this invention, it may be preferable to use one or more unlabeled or independently detectable probes in the assay to thereby suppress the binding of the pairs of probes to a non-target sequence. The presence of the "blocker probe(s)" helps to further increase the discrimination of the assay and thereby improve reliability and specificity.

Kits

In yet another embodiment, this invention is directed to kits suitable for performing an assay, which detects the presence, absence or amount of one or more target sequences, which may be present in a sample. The characteristics of the pairs of probes suitable for the detection, identification and/or quantitation of amount of one or more target sequence have been previously described herein. Furthermore, methods suitable for using the pairs of probes components of a kit to detect, identify or quantitate one or more target sequences, which may be present in a sample, have also been previously described herein.

The kits of this invention comprise one or more pairs of probes and other reagents or compositions, which are selected to perform an assay or otherwise simplify the performance of an assay. In another embodiment the kits contain pairs of probes, wherein each of at least two sets of probes are used to distinctly detect and distinguish between the two or more different target sequences which may be present in the sample. Thus, the pairs of probes are preferably labeled with independently detectable fluorophores so that each of the two or more different target sequences can be individually detected, identified or quantitated (a multiplex assay).

Exemplary Applications For Using The Invention:

The methods and kits of this invention are particularly useful for the detection, identification and/or quantitation of microorganisms in clinical samples, e.g. urine, blood, wounds, sputum, laryngeal swabs, gastric lavage, bronchial washings, biopsies, aspirates, expectorates as well as in food, beverages, water, pharmaceutical products, personal care products, dairy products or environmental samples and cultures thereof.

In another embodiment, the invention may be used to detect a target sequence which is specific for a genetically based disease or is specific for a predisposition to a genetically based disease. Non-limiting examples of diseases include, beta.-Thalassemia, sickle cell anemia, Factor-V Leiden, cystic fibrosis and cancer related targets such as p53, p10, BRC-1 and BRC-2.

In still another embodiment, the target sequence may be related to a chromosomal DNA, wherein the detection, identification or quantitation of the target sequence can be used in relation to forensic techniques such as prenatal screening, paternity testing, identity confirmation or crime investigation.

Having described the preferred embodiments of the invention, it will now become apparent to one of skill in the art that other embodiments incorporating the concepts described herein may be used. It is felt, therefore, that these embodiments should not be limited to disclosed embodiments but rather should be limited only by the spirit and scope of the following claims.

EXAMPLES

This invention is now illustrated by the following example, which is not intended to be limiting in any way.

Example 1

PNA Probe Sequence

Probe A    Flu-OO-GCT-TCT-CGT-CCG-TTC  (SEQ ID NO: 1)

Probe B    ACT-TCA-AAG-GAG-CAA-Lys-lys(Dabsyl)

(Note: O=8-amino-3,6-dioxaoctanoic acids; flu=5(6)-carboxy-fluorescein; Dabsyl=4-((-4-(dimethylamino)phenyl)azo)benzoic acid); Lys=Lysine Probe A is a fluorescein-labeled PNA probe targeting *Staphylococcus aureus* rRNA. The probe cross-hybridizes to *Staphylococcus schleiferi* rRNA where just a single mismatch exists to rRNA sequences of some *Staphylococcus schleiferi* strains (Oliveira et al. 2002. J. Clin. Microbiol. 40:247-251) as in FIG. 1.

Probe B is dabsyl-labeled PNA probe targeting *Staphylococcus schleiferi* rRNA adjacent to the target sequence for Probe A where 3 base differences exist between *Staphylococcus aureus* rRNA and *Staphylococcus schleiferi* rRNA.

Bacterium Strains.

Overnight cultures of bacterium strains representing *Staphylococcus aureus, Staphylococcus epidermidis, Staphylococcus haemolyticus* and *Staphylococcus scheiferi* were preparedby standard methods.

Preparation of Smears.

For each smear, one drop of PBS with 1% (v/v) Triton X-100 (Aldrich) was placed in a 8-mm diameter well of a teflon-coated microscope slide (Erie Scientific, Portsmouth, N.H.) and mixed gently with a small drop of re-suspended culture. The slide was then placed on a 55° C. slide warmer for 20 min at which point the smears were dry. Subsequently, the smears were disinfected by immersion into 96% (v/v) ethanol for 5-10 minutes and air-dried.

Fluorescence In situ Hybridization (FISH).

Smears were covered with approximately 20 µL of hybridization solution containing 10% (w/v) dextran sulfate (Sigma Chemical Co., St. Louis, Mo.), 10 mM NaCl (J. T. Baker), 30% (v/v) formamide (Sigma), 0.1% (w/v) sodium pyrophosphate (Sigma), 0.2% (w/v) polyvinylpyrrolidone (Sigma), 0.2% (w/v) ficoll (Sigma), 5 mM Na$_2$EDTA (Sigma), 1% (v/v) Triton X-100 (Aldrich), 50 mM Tris/HCl pH 7.5 and 500 nM Probe A with or without 500 nM Probe B. Coverslips were placed on the smears to ensure even coverage with hybridization solution, and the slides were subsequently placed on a slide warmer with a humidity chamber (Slidemoat, Boeckel, Germany) and incubated for 90 min at 55° C. Following hybridization, the coverslips were removed by submerging the slides into approximately 20 ml/slide pre-warmed 25 mM Tris, pH 10, 137 mM NaCl (J. T. Baker), 3 mM KCl (Sigma) in a water bath at 55° C. and washed for 30 min. Each smear was finally mounted using one drop of IMAGEN Mounting Fluid (DAKO, Ely, UK) and covered with a coverslip. Microscopic examination is conducted using a fluorescence microscope equipped with a FITC/Texas Red dual band filter set. The fluorescence intensity is scored: −: for no fluorescence intensity; +: for weak fluorescence intensity; ++: for medium fluorescence signal; +++: for strong fluorescence signal.

The results are listed in the table below and show how the use of Probe A and Probe B together quenches the fluorescence signal from hybridization of Probe A to *Staphylococcus schleiferi* hereby increasing the specificity for identification of *Staphylococcus aureus* as compared to the use of Probe A alone.

| Organism | Probe A | Probe A Probe B |
|---|---|---|
| *Staphylococcus aureus* | +++ | +++ |
| *Staphylococcus epidermidis* | − | − |
| *Staphylococcus haemolyticus* | − | − |
| *Staphylococcus schleiferi* | + | − |

It is envisioned that the fluorescent signal from hybridization of Probe A to *Staphylococcus* schleiferi rRNA is quenched by simultaneous hybridization with Probe B, whereas the signal from hybridization of Probe A to *Staphylococcus aureus* rRNA is unaffected because Probe B does not hybridize to *Staphylococcus aureus* rRNA due to the 3 base difference and will therefore not interfere with the fluorescent signal from *Staphylococcus aureus*, see FIG. 1.

This invention has been described in detail with reference to preferred embodiments thereof. However, it will be appreciated that those skilled in the art, upon consideration of this disclosure, may make modifications and improvements within the spirit and scope of the invention.

All references disclosed herein are incorporated by reference.

What is claimed is:

1. A method for the analysis of a target nucleotide sequence of interest in a sample, said method comprising:
   a. contacting the sample with at least one pair of probes (Probe A and Probe B),
   b. hybridizing Probe A and Probe B to the sample under hybridization conditions in which the desired degree of discrimination is achieved for an accurate result, wherein:
   i) Probe A comprises a nucleotide sequence which hybridizes under said hybridization conditions to both a target nucleotide sequence of interest and to a nucleotide sequence not of interest, and is labeled with a first fluorophore;
   ii) Probe B comprises a nucleotide sequence which hybridizes under said hybridization conditions to a nucleotide sequence not of interest adjacent the nucleotide sequence not of interest to which Probe A hybridizes, and is labeled with a quencher;
   c. detecting the hybridization of Probe A, wherein the fluorescence generated by the hybridization of Probe A to the nucleotide sequence not of interest is quenched by hybridization of probe B to the nucleotide sequence not of interest, and
   d. correlating the presence or amount of target nucleotide sequence of interest in the sample with the fluorescence generated upon hybridization of Probe A to the target nucleotide sequence of interest, wherein detection of the fluorescence of the fluorophore of Probe A is an indication of the presence or amount of the target nucleotide sequence of interest in said sample.

2. The method of claim 1, where the method is performed by fluorescence in situ hybridization.

3. The method of claim 1, wherein Probe A and Probe B are high affinity probes.

4. The method of claim 1, wherein Probe A and Probe B are peptide nucleic acid (PNA) probes.

5. The method of claim 1, wherein one of more of the probes has a probing nucleobase sequence of 11-16 subunits in length.

6. The method of claim 1, wherein Probe A comprises the following nucleotide sequence: GCT-TCT-CGT-CCG-TTC (SEQ ID NO: 1).

7. The method of claim 1 or 6, wherein Probe B comprises the following nucleotide sequence: ACT-TCA-AAG-GAG-CAA (SEQ ID NO: 2).

8. The method of claim 1, wherein Probe A consists essentially of the following nucleotide sequence: GCT-TCT-CGT-CCG-TTC (SEQ ID NO: 1) and the fluorophore.

9. The method of claim 1 or 6, wherein Probe B consists essentially of the following nucleotide sequence: ACT-TCA-AAG-GAG-CAA (SEQ ID NO: 2) and the quencher.

10. The method of claim 1, wherein Probe A consists of the following nucleotide sequence; GCT-TCT-CGT-CCG-TTC (SEQ ID NO: 1) and the fluorophore.

11. The method of claim 1, wherein Probe B consists of the following nucleotide sequence: ACT-TCA-AAG-GAG-CAA (SEQ ID NO: 1) and the quencher.

12. The method of claim 1, wherein Probe A is labeled with the fluorophore at a terminus closest to a hybridization site of Probe B, and Probe B is labeled with a quencher at a terminus closest to a hybridization site of Probe A.

13. The method of claim 1 or 12 wherein Probes A and B are labeled internally.

14. The method of claim 1, wherein Probe B further comprises a fluorophore at an opposite end from the quencher and wherein the fluorophore of Probe B comprises a different emission spectrum than the fluorophore of Probe A.

15. The method of claim 1, wherein, upon hybridization, probes A and B are separated by a distance of between from about one to about five nucleotide bases.

16. The method of claim 1, wherein the target sequence is obtained from a cell or tissue.

17. The method of claim 16, wherein the cell or tissue has been manipulated to preserve the target sequence therein.

18. The method of claim 17, wherein the manipulation includes fixation, freezing or desiccation.

19. The method of claim 1, wherein step (d) of the method detects, identifies, or quantitates the presence or amount of at least one species of a microorganism in the sample.

20. The method of claim 19, wherein the target nucleotide sequence is from a microorganism exposed to at least one antimicrobial agent and the presence or amount of target nucleotide sequence of interest is indicative of an effect of the antimicrobial agent on the microorganism.

21. The method of claim 1, wherein the presence or amount of the target nucleotide sequence of interest is indicative of a condition of medical interest.

22. The method of claim 1, wherein the hybridization of Probe B increases the specificity of the analysis of the target nucleotide sequence of interest.

* * * * *